United States Patent [19]

Chalmers et al.

[11] 4,317,450
[45] Mar. 2, 1982

[54] METHOD OF EPILATION

[76] Inventors: Edward Chalmers, 31 Benjamin Rd., Arlington, Mass. 02174; William H. Huggins, 26 Heritage Cir., Clinton, Conn. 06413

[21] Appl. No.: 42,799

[22] Filed: May 29, 1979

[51] Int. Cl.³ .............................................. A61B 17/41
[52] U.S. Cl. .......................... 128/303.13; 128/303.17
[58] Field of Search ...................... 128/303.13, 303.17, 128/303.18

[56] References Cited

U.S. PATENT DOCUMENTS

| | | | |
|---|---|---|---|
| 2,888,927 | 6/1959 | Fozard | 128/303.13 |
| 3,999,552 | 12/1976 | Huggins | 128/303.13 |
| 4,174,714 | 11/1979 | Mehl | 128/303.13 |

Primary Examiner—Lee S. Cohen

[57] ABSTRACT

An epilator system comprising the combination of an electric source for applying a regulated voltage to a region of a hair and a wetting solution with ionic properties. For hair removal, the wetting solution with ionic properties is applied to the hair down into the follicle to the papilla and preferably a high-frequency voltage lower than used in conventional epilators is then applied to the wetted hair.

16 Claims, 3 Drawing Figures

METHOD OF EPILATION

FIELD OF THE INVENTION

This invention relates to epilators for removal of hair.

BACKGROUND OF THE INVENTION

To permanently remove hair from a living being, it is necessary to stop hair growth at its source, the papilla located at the base of the hair follicle (a tubular aperture in the skin). It is known that an electric current applied to the papilla will coagulate it, and thus prevent it from initiating new growth. Conventional methods for applying the electric current are not reliable and often lead to painful burning of the skin and possible scarring. Two methods are presently in wide use. The oldest is referred to as electrolysis. In electrolysis, an attempt is made to precisely insert a thin needle into the individual hair follicle to the depth of the papilla, and a controlled RF voltage, sometimes as high as 200 volts, is applied. Skill is needed to properly locate the papilla, and improper needle insertion can be painful. Furthermore, some persons have curved or spiral hair follicles, making it especially difficult to locate the papilla.

The other conventional method, first disclosed in the Fozzard U.S. Pat. No. 2,888,927, replaces the needle with a tweezer which grasps the hair above the skin. A high RF voltage up to 800 volts is then applied for a period of 6 to 45 seconds. At the end of this time, the hair is supposed to release and slide out. Hair is not a good conductor of electricity, and thus it has been surmised that the method relies on capacitive coupling between the tweezers and the papilla. In practice, the method is less than 50 percent effective, and success seems to depend on the properties of the hair being removed.

Both conventional methods are time consuming and potentially painful should their high voltages be wrongly applied.

SUMMARY OF THE INVENTION

We have discovered an improved method of hair removal that is more effective, safer, and more easily performed than those presently known. A wetting solution with ionic properties is applied to the hair to create a conductive film along the hair down into the follicle to the papilla. A high-frequency voltage lower than used in conventional epilators is then applied to the wetted hair.

In preferred embodiments, the wetting solution is selected such that when the applied solution is subjected to a difference in potential, the charged particles (ions) will establish a conductive path from tweezer tips, which are grasping the hair just above the skin, down to the papilla. The ionic strength of the solution can vary, the limits being dependent to some degree on individual factors such as the natural conductivity of the hair of the user. For our purpose a good guide for selecting the current-carrying ability of the solution is that it have a conductivity equivalent to 5 to 25 ppm Sodium Chloride in solution. This solution should have sufficient current-carrying capability for removal of hair from a wide range of individuals.

For selecting a solution with sufficient wettability normally, a wetting liquid is evaluated by observing its surface tension. Theoretically this is measured by the angle of the tangent in the surface of the liquid at the point of contact with a solid surface. For our purpose, it is sufficient to approximately indicate the surface tension of a preferred wetting solution as follows: If a drop with about 1/20 ml volume spreads across about 5 square centimeters to give about 0.1 mm film thickness it should have sufficient wettability to establish the required film.

Another aspect of this invention concerns the particular solutions employed, which include both wetting agents or surfactants and compounds which provide ions in the solutions. Suitable wetting agents include such water-soluble nonionized surfactants as polyoxy ethylene oleyl ether. Preferred for use in the system of this invention, however, are compounds such a lauryl sulfate salts which are long chain substances with ionizable end groups. The latter compounds in appropriate solution can satisfactorily provide both the film path to the papilla and the ions to transport the electric energy from the RF source along that path to the roots of the hair being treated.

The most effective systems include solutions of ionizable surfactants such as the lauryl sulfate salts with additional ion-providing substances as quaternary nitrogen compounds and/or diethanol amines.

The oiliness of skin may vary from person to person and in different areas of the body. The chosen surfactants additionally contribute to the efficacy of the system by considerably decreasing the oil-water interfacial tension thereby creating a detergent effect. This removes oil from the hair surface and thereby aids in directing the RF energy to the hair root.

The conductivity of the path provided by the solution along a hair will decay after a time interval of no greater than 20 seconds, preferably approximately 2 to 10 seconds, thereby limiting the amount of current flowing to the body to prevent burns. During this short interval, the solution delivers an effective current to the papilla, in all likelihood the majority of the current flowing to the papilla rather than to the surrounding follicle wall and skin. In the beginning, as current begins to flow it is probable that a slight warming of the follicle by the current tends to open the follicle to facilitate penetration of the solution to the papilla, and the thin film of liquid available at the surface flows into the follicle until it is depleted.

PREFERRED EMBODIMENT

A preferred embodiment of the invention will now be described, after first briefly describing the drawings.

Figure 1:
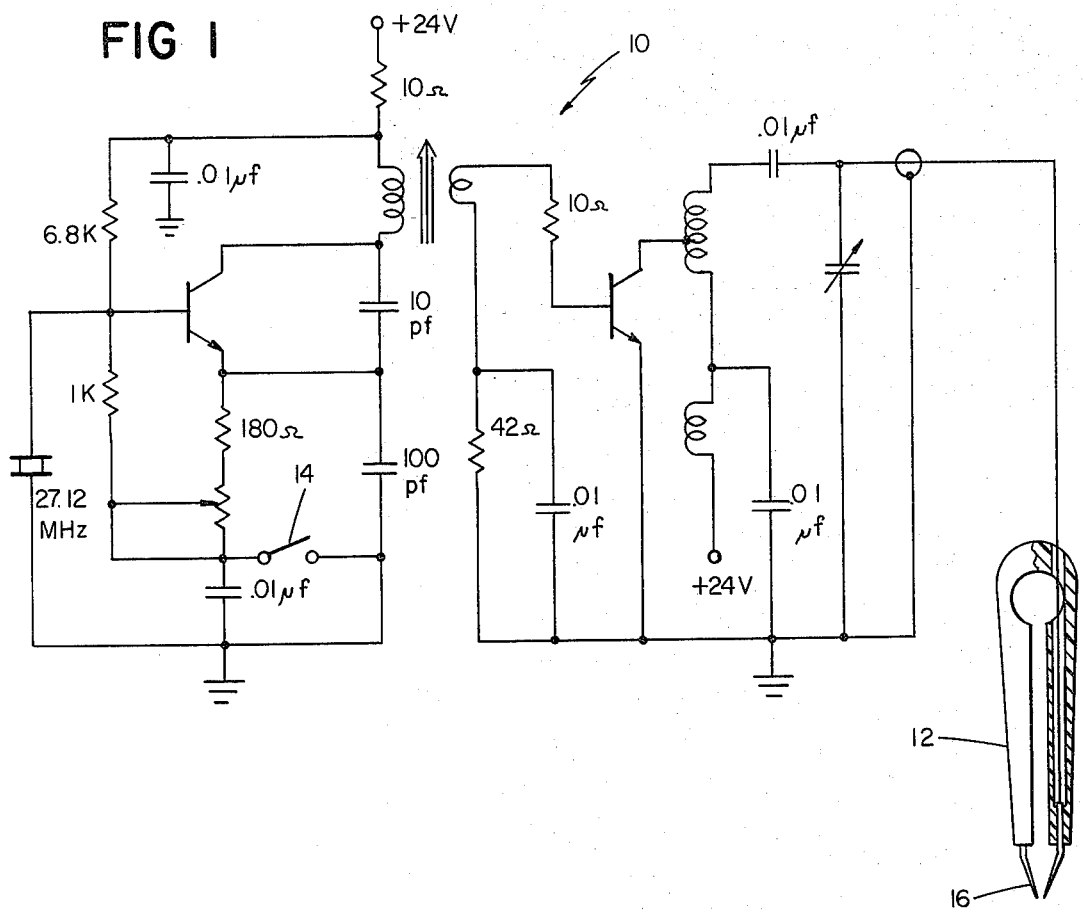
FIG. 1 is a circuit schematic of the high-frequency voltage generator and a diagrammatic view of the tweezers for grasping a hair.

Referring to FIG. 1, there is shown a typical high-frequency (27.120 megahertz) voltage generator 10 for producing a low-power output at tweezer 12. The maximum power delivered by the tweezer is limited by the power output of the generator, which is about 1.2 watts. The generator supplies an RF voltage in the range of 50 to 80 VAC when a foot pedal switch 14 is closed. Tweezer 12 is molded from plastic to provide insulation, and the voltage is carried to the tweezers by a coaxial cable whose length is selected to maximize power transfer to the tweezers.

Figure 2:
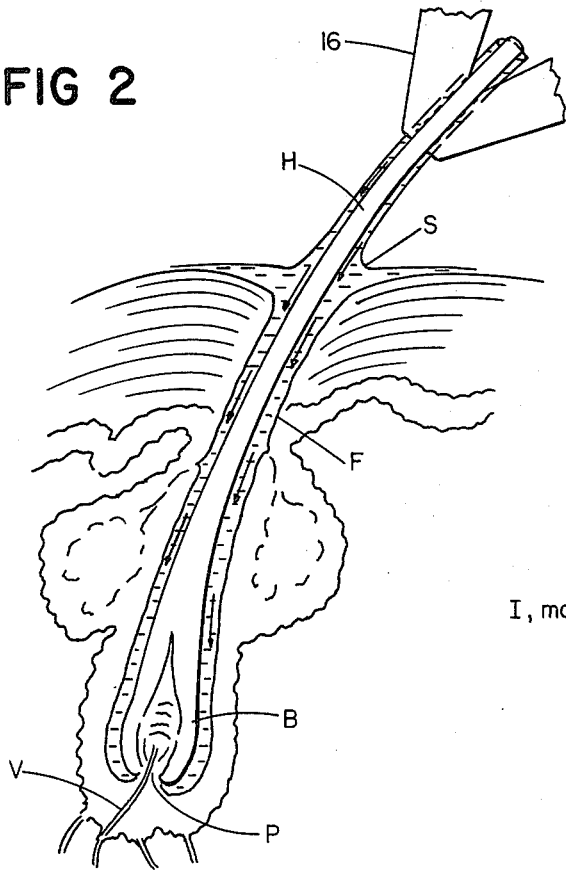
FIG. 2 is a cross-sectional view of a human hair growing in a skin follicle. It shows the solution of the invention in place around the hair both inside and outside the follicle, and indicates current flow to the hair bulb by arrows.

Referring to FIG. 2, the tip 16 of tweezer 12 grasps a human hair H at about 1/16 inch above the skin level. (The Figure shows the tweezers somewhat closer than 1/16 inch.) A human hair grows in a tube-like follicle F about 1/16 to ⅛ inch deep. At the bottom of the follicle, the hair bulb B fits over the papilla P. Nourishment reaches the papilla through blood vessels V. Coagulation of the papilla will prevent regrowth of the hair.

To remove hair, the wetting, ionic solution S is applied to an area of the skin where the hair has been scissorcut to leave only short stubs. After a few seconds, long enough for the solution to form a conductive film along the hair, the hair is grasped by tweezer 12, and power is applied to the tweezer by depressing foot switch 14.

Figure 3:
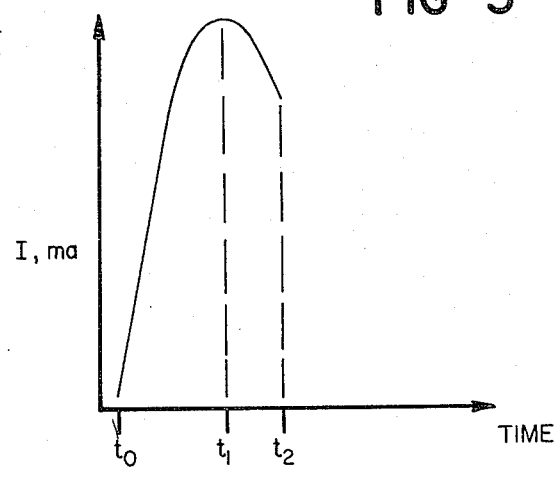
FIG. 3 is a plot of the variation in current supplied by the tweezer during a typical hair removal cycle.

A typical plot of current versus time after the foot switch is depressed at time $t_0$ is given in FIG. 3. Initially, current rises rapidly to a maximum at time $t_1$ which is about 10 ma. Then, after a brief interval of approximately 2 seconds (time $t_2$) the current decays, and, as the treated hair slides out under tension by the tweezer, the conductive interval ceases.

It is thought that this phenomena, which provides a built-in check against burning by limiting the duration of current flow, is caused by movement of the solution within the follicle. The follicle is normally closed around the hair. The current flow tends to slightly warm the follicle and cause it to open to aid penetration of the solution. As the solution works down the follicle and approaches the papilla, the blood vessels V provide a better conductive path than do the follicle walls, and thus the current tends to increase to a maximum at $t_1$ in FIG. 3. The excellent conductive path provided by the solution to the papilla and by the blood vessels beyond the papilla assure that a concentration of current flows through the papilla rather than the follicle walls, which are coated with oils and thus are less conductive, and thus enough energy is supplied to the papilla to coagulate it.

It is thought that the rapid decay of the current curve is the result of an interruption in the conductive path rather than a change in the chemical composition of the liquid (although the latter may be a contributing factor). The conductive path could be broken either by the papilla being coagulated and thus separated from the highly-conductive blood vessels or by a break or stretching out and thinning of the conductive film provided by the solution.

With further reference to the current curve, at time $t_2$, the papilla is coagulated, and the hair can be easily removed from the same wetted area without adding additional solution. Eventually, though, the solution is absorbed by follicles and other pores, and more must be applied.

Other embodiments of the invention are within the following claims. For example, many other solutions having the necessary conductive and wetting properties could be substituted for the disclosed solutions, and different electrical voltage generators could be employed. Also the frequency of the generator might be other than 27.120 megahertz. This frequency has been selected because it is a typical medical frequency.

What is claimed is:

1. A method of removing a hair from a living being comprising the steps of:

selecting an ionic, wetting solution for the hair and surrounding skin,
   said solution selected to be nontoxic, having ions in quantities sufficient, in a thin film, to conduct an electrical current of sufficient strength to coagulate a hair papilla and having wetting properties sufficient to wet the external hair and the hair within the follicle to form a continuous thin film of solution therealong to thereby establish an ion path from a voltage-applying region on the hair above the skin to a region within the follicle, through which path electrical current can flow,
   applying said solution to the hair and surrounding skin,
   allowing sufficient time to pass to permit said solution to form said continuous film, and
   applying a regulated electric voltage to said hair at said region thereby to cause electric current to flow from said region down said film to the hair papilla and thence to the interior body of the living being,
   said electric voltage being regulated in respect of said liquid to establish a current sufficient to coagulate said hair papilla, and thereafter removing said hair.

2. The method of claim 1 wherein said solution is selected to cause current flow to substantially cease after expiration of an interval no greater than 20 seconds.

3. The method of claim 2 wherein said current flow exhibits a pattern over time, wherein the current flow rises to a maximum during a first interval and then decreases rapidly and terminates during a second interval.

4. The method of claim 2 wherein said cessation of current flow is achieved by selecting the wetting properties of said solution such that the thickness of said film is limited sufficiently to limit the supply of solution at the vicinity of the hair to only that needed to fill the follicle whereby current flow is retarded by a thinning out of said film along the hair after said solution has worked fully down into the follicle and the papilla has been coagulated.

5. The method of claim 4 wherein said wetting properties are selected to cause a drop of said solution to spread over an area of skin to a depth of the order of 0.1 mm.

6. The method of claim 2 wherein said interval is between 2 and 10 seconds.

7. The method of claim 1 wherein the ions of said solution are provided by organic wetting agents.

8. The method of claim 7 wherein said wetting agents include lauryl sulfate salts.

9. The method of claim 7 wherein said wetting agents include diethanol amines.

10. The method of claim 7 wherein said wetting agents include quaternary nitrogen compounds which provide ions in solution.

11. The method of claim 1 wherein said solution is selected such that, during an interval following said application of voltage, the majority of current is delivered to the hair papilla rather than to the surrounding follicle wall.

12. The method of claim 1 wherein said voltage is applied to the hair by a contacting device contacting the hair at said region.

13. The method of claim 12 wherein said voltage is applied to the hair with a tweezer grasping the hair at said region.

14. The method of claim 1 wherein, due to the utilization of an ionic wetting solution, said regulated voltage is below about 80 volts.

15. The method of claim 1 wherein, due to the utilization of an ionic wetting solution, said electric current is about 10 ma.

16. The method of claim 1 wherein said solution has a conductivity equivalent to 5 to 25 ppm sodium chloride in solution.

* * * * *